(12) United States Patent
Bulatov et al.

(10) Patent No.: US 12,167,927 B2
(45) Date of Patent: Dec. 17, 2024

(54) REAL-TIME MONITORED COMPUTED TOMOGRAPHY (CT) RECONSTRUCTION FOR REDUCING RADIATION DOSE

(71) Applicant: Smart Engines Service, LLC, Moscow (RU)

(72) Inventors: Konstantin Bulatovich Bulatov, Moscow (RU); Anastasia Sergeevna Ingacheva, Kazan (RU); Marat Irikovich Gilmanov, Belebey (RU); Marina Valerievna Chukalina, Moscow (RU); Vladimir Viktorovich Arlazarov, Moscow (RU); Dmitry Petrovich Nikolaev, Moscow (RU)

(73) Assignee: Smart Engines Service, LLC, Moscow (RU)

( * ) Notice: Subject to any disclaimer, the term of this patent is extended or adjusted under 35 U.S.C. 154(b) by 336 days.

(21) Appl. No.: 17/883,837

(22) Filed: Aug. 9, 2022

(65) Prior Publication Data

US 2023/0233171 A1 Jul. 27, 2023

Related U.S. Application Data

(63) Continuation of application No. PCT/RU2022/000018, filed on Jan. 21, 2022.

(51) Int. Cl.
*A61B 6/03* (2006.01)
*A61B 6/00* (2006.01)
(Continued)

(52) U.S. Cl.
CPC ............. *A61B 6/542* (2013.01); *A61B 6/027* (2013.01); *A61B 6/032* (2013.01); *A61B 6/5217* (2013.01);
(Continued)

(58) Field of Classification Search
CPC ....... A61B 6/027; A61B 6/032; A61B 6/5217; A61B 6/542; G06T 7/0012; G06T 11/006;
(Continued)

(56) References Cited

U.S. PATENT DOCUMENTS

| 7,751,607 | B2 | 7/2010 | Reeves et al. |
| 9,466,133 | B2 | 10/2016 | Sowards-Emmerd et al. |

(Continued)

OTHER PUBLICATIONS

Amyar et al., "Multi-task deep learning based CT imaging analysis for COVID-19 pneumonia: Classification and segmentation," Computers in Biology and Medicine 126 (2020) 104037, 11 pages.
(Continued)

*Primary Examiner* — Mark R Gaworecki
(74) *Attorney, Agent, or Firm* — Procopio, Cory, Hargreaves & Savitch LLP

(57) ABSTRACT

Real-time monitored computed tomography (CT) reconstruction for reducing a radiation does. During helical CT scanning of a target object, projections may be acquired in either a full mode which subjects the target object to a full radiation dose, or a reduced mode which subjects the target object to a reduced radiation dose (e.g., by reducing the number of projections acquired, reducing the exposure time, etc.). After a sector is acquired in the full mode, a slice of the target object that is influenced by that sector is identified, and a CT image of that slice is reconstructed using projections that have been previously acquired for that slice. When a stopping rule is satisfied based on this partial reconstruction, the full mode is switched to the reduced mode, and at least one subsequent sector is acquired in the reduced mode.

17 Claims, 6 Drawing Sheets

(51) Int. Cl.
- A61B 6/02 (2006.01)
- G06T 7/00 (2017.01)
- G06T 11/00 (2006.01)

(52) U.S. Cl.
CPC .......... *G06T 7/0012* (2013.01); *G06T 11/006* (2013.01); *G06T 2207/10081* (2013.01); *G06T 2207/20084* (2013.01); *G06T 2207/30061* (2013.01); *G06T 2211/441* (2023.08)

(58) Field of Classification Search
CPC . G06T 2207/10081; G06T 2207/20084; G06T 2207/30061; G06T 2211/411
See application file for complete search history.

(56) References Cited

U.S. PATENT DOCUMENTS

| 2019/0069868 A1* | 3/2019 | Goto | A61B 6/027 |
| 2019/0125290 A1* | 5/2019 | Arai | A61B 6/545 |

OTHER PUBLICATIONS

Anirudh et al., "Lose The Views: Limited Angle CT Reconstruction via Implicit Sinogram Completion," arXiv:1711.10388v3 [cs.CV] Jul. 11, 2018, 16 pages.
Brodeur et al., "A literature review of the economics of COVID-19," J Econ Surv. 2021, pp. 1-38.
Bruder et al., "Single-Slice Rebinning Reconstruction in Spiral Cone-Beam Computed Tomography," IEEE Transactions on Medical Imaging, vol. 19, No. 9, Sep. 2000, pp. 873-887.
Bulatov et al., "Monitored Reconstruction: Computed Tomography as an Anytime Algorithm," IEEE Access, Jun. 12, 2020, 16 pgs.
Bulatov et al., "Monitored Tomographic Reconstruction—An Advanced Tool to Study the 3D Morphology of Nanomaterials," Nanomaterials 2021, 11 pgs.
Dixon et al., "Spiral CT: how much does radiation dose matter?", The Lancet, vol. 352, Oct. 3, 1998, 2 pgs.
Flohr et al., "Image reconstruction and image quality evaluation for a 16-slice CT scanner," Medical Physics, vol. 30, No. 5, May 2003, pp. 832-845.
Peter Gilbert, "Iterative Methods for Three-dimensional Reconstruction of an Object from Projections," J. Theor. Biol., (1972) 36, pp. 105-117.
Hani et al., "COVID-19 pneumonia: A review of typical CT findings and differential diagnosis," Diagnostic and Interventional Imaging 101 (2020), pp. 263-268.
Hsieh et al., "Computed tomography recent history and future perspectives," Journal of Medical Imaging, Sep./Oct. 2021, vol. 8(5), 24 pgs.
Hu et al., "Weakly Supervised Deep Learning for COVID-19 Infection Detection and Classification from CT Images," IEEE Access, vol. 8, Jun. 29, 2020, 21 pgs.
Kalender et al., "Spiral Volumetric CT with Single-Breath-Hold Technique, Continuous Transport, and Continuous Scanner Rotation," Thoracic Radiology, 1990, vol. 176, pp. 181-183.
Matenine et al., "Potential of iterative reconstruction for maxillofacial cone beam CT imaging: technical note," Neuroradiology (2020) 62:1511-1514.
Oh et al., "Deep Learning COVID-19 Features on CXR Using Limited Training Data Sets," IEEE Transactions on Medical Imaging, vol. 39, No. 8, Aug. 2020, pp. 2688-2700.
Palenstijn et al., "Performance improvements for iterative electron tomography reconstruction using graphics processing units (GPUs)," Journal of Structural Biology 176 (2011) pp. 250-253.
Polacin et al., "Evaluation of Section Sensitivity Profiles and Image Noise in Spiral CT," Radiology 1992; 185:29-35.
Rahimzadeh et al., "A fully automated deep learning-based network for detecting COVID-19 from a new and large lung CT scan dataset," Biomedical Signal Processing and Control 68 (2021) 102588, 15 pgs.
Schöndube et al., "Exact Efficient Handling of Interrupted Illumination in Helical Cone-Beam Computed Tomography with Arbitrary Pitch," Tsinghua Sci Technol. Feb. 2010 ; 15(1): 36-43. doi: 10.1016/S1007-0214(10)70006-7, 16 pgs.
Scott et al., "Process imaging for automatic control," CRC Press, 2018, entire book.
Rebecca Smith-Bindman, "CT Radiation and the Risk of Cancer," Curr Radiol Rep (2015) 3:3, 7 pgs.
Talha et al., "Novel FBP based sparse-view CT reconstruction scheme using self-shaping spatial filter based morphological operations and scaled reprojections," Biomedical Signal Processing and Control 64 (2021) 102323, 15 pgs.
Aarle et al., "Fast and flexible X-ray tomography using the ASTRA toolbox," Optics express 24.22 (2016): 25129-25147, 19 pgs.
Aarle et al., "The ASTRA Toolbox: A platform for advanced algorithm development in electron tomography," Ultramicroscopy 157 (2015): pp. 35-47.
Villarraga-Gómez et al., "Effect of the number of projections on dimensional measurements with X-ray computed tomography," Precision Engineering 66 (2020): 445-456.
Wang et al., "FocalMix: Semi-Supervised Learning for 3D Medical Image Detection," Proceedings of the IEEE/CVF Conference on Computer Vision and Pattern Recognition, 2020, 10 pgs.
K.S. White, "Invited article: helical/spiral CT scanning: a pediatric radiology perspective," Pediatr Radiol. 1996;26(1): pp. 5-14.
Wiest et al., "CT Scanning: A Major Source of Radiation Exposure," Seminars in Ultrasound CT, and MRI, vol. 23, No. 5 Oct. 2002, pp. 402-410.
Ying et al., "X2CT-GAN: Reconstructing CT from Biplanar X-Rays with Generative Adversarial Networks," arXiv:1905.06902v1 [eess.IV] May 16, 2019, 13 pgs.
Zhang et al., "Metalnv-Net: Meta Inversion Network for Sparse View CT Image Reconstruction," IEEE Transactions on Medical Imaging, vol. 40, No. 2, Feb. 2021, pp. 621-634.
Zhang et al., "DoDNet: Learning to segment multi-organ and tumors from multiple partially labeled datasets," arXiv:2011.10217v1 [cs.CV] Nov. 20, 2020, pp. 1-10.
Zheng et al,. "Deep Learning-based Detection for COVID-19 from Chest CT using Weak Label." MedRxiv (2020), pp. 1-13.
Zhou et al. "Collaborative Learning of Semi-Supervised Segmentation and Classification for Medical Images," Proceedings of the IEEE/CVF conference on computer vision and pattern recognition, 2019, pp. 2079-2088.
Filatova et al., "Opportunities to reduce the radiation exposure during computed tomography to assess the changes In the lungs in patients with COVID-19: use of adaptive statistical iterative reconstruction," Digital Diagnostics. 2021;2 (2):94-104. DOI: https://doi.org/10.17816/DD62477.
International Search Report and Written Opinion for PCT/RU2022/000018 mailed on Oct. 13, 2022, 9 pages.

* cited by examiner

REAL-TIME MONITORED COMPUTED TOMOGRAPHY (CT) RECONSTRUCTION FOR REDUCING RADIATION DOSE

BACKGROUND

Field of the Invention

The embodiments described herein are generally directed to computed tomography (CT), and, more particularly, to using real-time monitored CT reconstruction during helical CT imaging to reduce the radiation dose to the target object (e.g., of a subject).

Description of the Related Art

Computed tomography (CT) is on the front lines of medical diagnostic imaging. Methods of X-ray computed tomography continue to evolve, along with methods of automated medical image analysis. The introduction of helical computed tomography in the early 1990's has provided the conditions necessary for quick scanning of complete organs, such as the lungs or other sections of a subject's body. In helical computed tomography, a subject (e.g., human patient) is moved slowly through a gantry, on which an X-ray source (e.g., X-ray tube) is rotationally mounted, during continuous rotation of the X-ray source around the subject. Thus, the X-ray tube traverses a helical trajectory around the subject, as illustrated in FIG. 1. The X-rays are detected by detectors that are mounted on the gantry, opposite the X-ray tube. The scanning quality associated with the movement of the table feed through the gantry have been studied, and multiple CT reconstruction algorithms have been proposed to work with this helical CT scanning process. See, e.g., Bruder et al., "Single-slice Rebinning Reconstruction in Spiral Cone-beam Computed Tomography," IEEE Trans. Med. Imaging, 19(9):873-887, 2000, PMID: 11127602; and Schondube et al., "Exact Efficient Handling of Interrupted Illumination in Helical Cone-Beam Computed Tomography with Arbitrary Pitch," Tsinghua Sci. Technol., 15(1):36-43, 2010; which are both hereby incorporated herein by reference as if set forth in full.

Computed tomography is a powerful tool for medical examination, and plays a particularly important role in the investigation of acute diseases, such as the coronavirus disease 2019 (COVID-19). However, helical computed tomography requires several radiology specialists to manually inspect each scanning result. Shortages of medical staff, resulting from the global pandemic, presented the need for automated methods of COVID-19 screening.

Deep-learning frameworks are capable of detecting and localizing lesions in CT scans. Thus, a deep-learning-based model for automated COVID-19 detection in chest CT scans has been developed, as described, for example, in Zhang et al., "DoDNet: Learning to Segment Multi-Organ and Tumors from Multiple Partially Labeled Datasets," in Computer Vision and Pattern Recognition (CVPR), pp. 1195-1204, 2021, which is hereby incorporated herein by reference as if set forth in full. The DoDNet algorithm achieved sensitivity and specificity values greater than 0.9, rendering it clinically applicable. Rahimzadeh et al., "A Fully Automated Deep Learning-Based Network for Detecting COVID-19 from a New and Large Lung CT Scan Dataset," Biomedical Signal Processing and Control, 68:102588, 2021, which is hereby incorporated herein by reference as if set forth in full, presented a high-speed system for accurate and fully automated COVID-19 detection from chest CT scans. This system could work with three different neural network (NN) models: Xception, ResNet50 v2, and Feature Pyramid Network (FPN). In the classification stage for a single image of a slice, the FPN model achieved 98.49% accuracy on more than 7,996 test images.

However, CT scans require radiation exposure, which in modern doses may contribute to the occurrence of cancer. The total radiation dose for a CT scan is proportional to the number of projections collected, radiation intensity, and exposure time. While efforts have been made to achieve reductions in each of these contributors, such reductions inevitably lead to lower image quality. Different approaches to the reconstruction phase have been developed to compensate for this loss in image quality, as well as to address an increase in image artifacts. See, e.g., Matenine et al., "Potential of Iterative Reconstruction for Maxillofacial Cone Beam CT Imaging: Technical Note," Neuroradiology, 62(11):1511-1514, 2020; Talha et al., "Novel FBP Based Sparse-View CT Reconstruction Scheme Using Self-Shaping Spatial Filter Based Morphological Operations and Scaled Reprojections," Biomedical Signal Processing and Control, 64:102323, 2021; and Villarraga-Gómez et al., "Effect of the Number of Projections on Dimensional Measurements with X-ray Computed Tomography," Precision Engineering, 66:445-456, 2020; which are all hereby incorporated herein by reference as if set forth in full. These approaches include utilizing deep learning for regularization, predicting missing projections, and performing reconstruction from two orthogonal X-rays using a generative adversarial network. See Zhang et al., "MetaInv-Net: Meta Inversion Network for Sparse View CT Image Reconstruction," IEEE Transactions on Medical Imaging, 40(2):621-634, 2021; Anirudh et al., "Lose the Views: Limited Angle CT Reconstruction via Implicit Sinogram Completion," in CVPR, pp. 6343-6352, 2018; and Ying et al., "X2CT-GAN: Reconstructing CT from Biplanar X-rays with Generative Adversarial Networks," in CVPR, pp. 10619-10628, 2019; which are all hereby incorporated herein by reference as if set forth in full.

All of these approaches to dose reduction represent fixed scanning protocols. One serious disadvantage of a fixed scanning protocol is that the quality of reconstruction is not known until the very end of the acquisition process, i.e., after the whole radiation dose has already been administered. This means that, if the reconstructed CT image does not have acceptable image quality (i.e., due to too much dose reduction), the CT scan will have to be repeated, thereby increasing the total radiation dose to which the subject is exposed.

SUMMARY

Accordingly, systems, methods, and non-transitory computer-readable media are disclosed for using real-time monitored CT reconstruction during helical CT imaging to reduce a radiation dose.

In an embodiment, a method comprises using at least one hardware processor to, during helical computed tomography (CT) scanning of a target object, after acquiring a set of projections from a sector in a full mode which subjects the target object to a first radiation dose: identify a slice of the target object that is influenced by the sector; reconstruct a CT image of the identified slice using projections that have been previously acquired for the slice; determine whether or not a stopping rule is satisfied based on the reconstructed CT image; and, when determining that the stopping rule is satisfied, switch from the full mode to a reduced mode which subjects the target object to a second radiation dose, wherein the second radiation dose is less than the first radiation dose, and acquire a set of projections from at least one subsequent sector in the reduced mode.

The method may further comprise using the at least one hardware processor to, when determining that the stopping rule is satisfied, determine a next sector that corresponds to a next slice of the target object, wherein acquiring a set of projections from at least one subsequent sector in the reduced mode comprises acquiring a set of projections from each subsequent sector in the reduced mode until the determined next sector, and switching from the reduced mode to the full mode prior to acquiring a set of projections from the determined next sector. Determining a next sector that corresponds to a start of a next slice of the target object may comprise identifying a lowest indexed sector that influences the next slice.

Identifying a slice of the target object that is influenced by the sector may comprise identifying a first slice, along a trajectory of the helical CT scanning, in a range of slices that are influenced by the sector based on a geometry of the helical CT scanning.

Determining whether or not a stopping rule is satisfied based on the reconstructed CT image may comprise: applying a classification model to the reconstructed CT image to produce a membership estimation representing a probability that the reconstructed CT image is a member of one of a plurality of classes; and determining whether or not the stopping rule is satisfied based on the membership estimation. Determining whether or not the stopping rule is satisfied based on the membership estimation may comprise: when the membership estimation exceeds a prediction threshold at least once within an initial subset of sectors consisting of a first threshold number of sectors, determining that the stopping rule is satisfied when the first threshold number of sectors have been acquired; and, when the membership estimation never exceeds the prediction threshold within the initial subset of sectors, determining that the stopping rule is satisfied when a second threshold number of sectors have been acquired following an initial sector for which the membership estimation of the reconstructed CT image exceeds the prediction threshold. The plurality of classes may comprise a first class representing an absence of an anomaly, and a second class representing a presence of an anomaly. The anomaly may be COVID-19. The target object may comprise at least one lung of a subject (e.g., human subject). The classification model may comprise a neural network. The neural network may be a deep-learning neural network. The neural network may be a Feature Pyramid Network (FPN).

The full mode may acquire a first number of projections, whereas the reduced mode acquires a second number of projections that is less than the first number. The second number may be at least 20% less than the first number.

The full mode may acquire each projection using a first exposure time, whereas the reduced mode acquires each projection using a second exposure time that is shorter than the first exposure time.

Any of the methods may be embodied in executable software modules of a processor-based system (e.g., CT scanning system), such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems, methods, and non-transitory computer-readable media are disclosed for using real-time monitored CT reconstruction during helical CT imaging to reduce a radiation dose. After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System Overview

Figure 2:
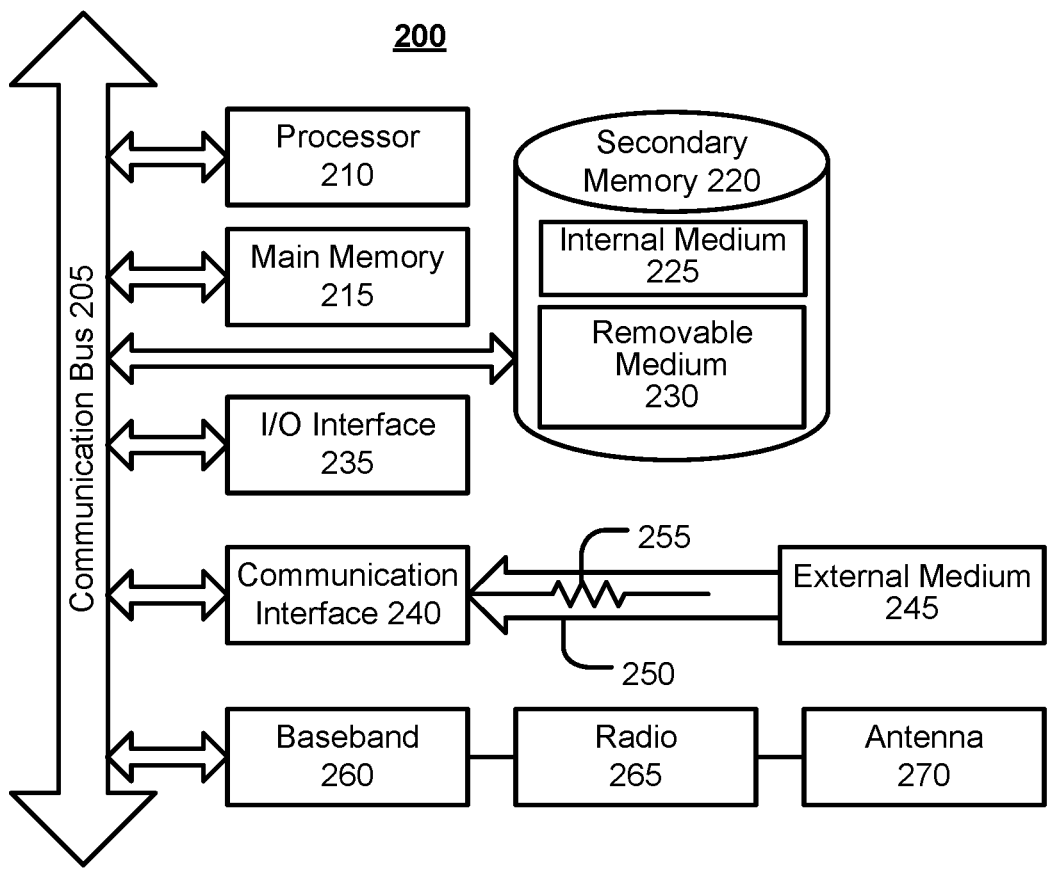
FIG. 2 illustrates an example processing system, by which one or more of the processes described herein, may be executed, according to an embodiment.

FIG. 2 is a block diagram illustrating an example wired or wireless system 200 that may be used in connection with various embodiments described herein. For example, system 200 may be used as or in conjunction with one or more of the functions, processes, or methods (e.g., to store and/or execute the software) described herein. System 200 can be a server or any conventional personal computer, or any other processor-enabled device that is capable of wired or wireless data communication. Other computer systems and/or architectures may be also used, as will be clear to those skilled in the art.

System 200 preferably includes one or more processors 210. Processor(s) 210 may comprise a central processing unit (CPU). Additional processors may be provided, such as a graphics processing unit (GPU), an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 210. Examples of processors which may be used with system 200 include, without limitation, any of the processors (e.g., Pentium™, Core i7™, Xeon™, etc.) available from Intel Corporation of Santa Clara, California, any of the processors available from Advanced Micro Devices, Incorporated (AMD) of Santa Clara, California, any of the processors (e.g., A series, M series, etc.) available from Apple Inc. of Cupertino, any of the processors (e.g., Exynos™) available from Samsung Electronics Co., Ltd., of Seoul, South Korea, any of the processors available from NXP Semiconductors N.V. of Eindhoven, Netherlands, and/or the like.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 200 preferably includes a main memory 215 and may also include a secondary memory 220. Main memory 215 provides storage of instructions and data for programs executing on processor 210, such as any of the software discussed herein. It should be understood that programs stored in the memory and executed by processor 210 may be written and/or compiled according to any suitable language, including without limitation C/C++, Java, JavaScript, Perl, Visual Basic, NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 is a non-transitory computer-readable medium having computer-executable code (e.g., any of the software disclosed herein) and/or other data stored thereon. The computer software or data stored on secondary memory 220 is read into main memory 215 for execution by processor 210. Secondary memory 220 may include, for example, semiconductor-based memory, such as programmable read-only memory (PROM), erasable programmable read-only memory (EPROM), electrically erasable read-only memory (EEPROM), and flash memory (block-oriented memory similar to EEPROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

In alternative embodiments, secondary memory 220 may include other similar means for allowing computer programs or other data or instructions to be loaded into system 200. Such means may include, for example, a communication interface 240, which allows software and data to be transferred from external storage medium 245 to system 200. Examples of external storage medium 245 include an external hard disk drive, an external optical drive, an external magneto-optical drive, and/or the like.

As mentioned above, system 200 may include a communication interface 240. Communication interface 240 allows software and data to be transferred between system 200 and external devices (e.g. printers), networks, or other information sources. For example, computer software or executable code may be transferred to system 200 from a network server via communication interface 240. Examples of communication interface 240 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network or another computing device. Communication interface 240 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 240 are generally in the form of electrical communication signals 255. These signals 255 may be provided to communication interface 240 via a communication channel 250. In an embodiment, communication channel 250 may be a wired or wireless network, or any variety of other communication links. Communication channel 250 carries signals 255 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed software) is stored in main memory 215 and/or secondary memory 220. Computer-executable code can also be received via communication interface 240 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 245), and any peripheral device communicatively coupled with communication interface 240 (including a network information server or other network device). These non-transitory computer-readable media are means for providing software and/or other data to system 200.

In an embodiment that is implemented using software, the software may be stored on a computer-readable medium and loaded into system 200 by way of removable medium 230, I/O interface 235, or communication interface 240. In such an embodiment, the software is loaded into system 200 in the form of electrical communication signals 255. The software, when executed by processor 210, preferably causes processor 210 to perform one or more of the processes and functions described elsewhere herein.

In an embodiment, I/O interface 235 provides an interface between one or more components of system 200 and one or more input and/or output devices. Example input devices include, without limitation, sensors, keyboards, touch screens or other touch-sensitive devices, cameras, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 200 may also include optional wireless communication components that facilitate wireless communication over a voice network and/or a data network. The wireless communication components comprise an antenna system 270, a radio system 265, and a baseband system 260. In system 200, radio frequency (RF) signals are transmitted and received over the air by antenna system 270 under the management of radio system 265.

In an embodiment, antenna system 270 may comprise one or more antennae and one or more multiplexors (not shown) that perform a switching function to provide antenna system 270 with transmit and receive signal paths. In the receive path, received RF signals can be coupled from a multiplexor to a low noise amplifier (not shown) that amplifies the received RF signal and sends the amplified signal to radio system 265.

In an alternative embodiment, radio system 265 may comprise one or more radios that are configured to communicate over various frequencies. In an embodiment, radio system 265 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 265 to baseband system 260.

If the received signal contains audio information, then baseband system 260 decodes the signal and converts it to an analog signal. Then the signal is amplified and sent to a speaker. Baseband system 260 also receives analog audio signals from a microphone. These analog audio signals are converted to digital signals and encoded by baseband system 260. Baseband system 260 also encodes the digital signals for transmission and generates a baseband transmit audio signal that is routed to the modulator portion of radio system 265. The modulator mixes the baseband transmit audio signal with an RF carrier signal, generating an RF transmit signal that is routed to antenna system 270 and may pass through a power amplifier (not shown). The power amplifier amplifies the RF transmit signal and routes it to antenna system 270, where the signal is switched to the antenna port for transmission.

Baseband system 260 is also communicatively coupled with processor(s) 210. Processor(s) 210 may have access to data storage areas 215 and 220. Processor(s) 210 are preferably configured to execute instructions (i.e., computer programs, such as the disclosed software) that can be stored in main memory 215 or secondary memory 220. Computer programs can also be received from baseband processor 260 and stored in main memory 210 or in secondary memory 220, or executed upon receipt. Such computer programs, when executed, can enable system 200 to perform the various functions of the disclosed embodiments.

2. Process Overview

Embodiments of processes for using real-time monitored CT reconstruction during helical CT imaging to reduce a radiation dose will now be described in detail. It should be understood that the described processes may be embodied in one or more software modules that are executed by one or more hardware processors (e.g., processor 210), for example, as a computer program or software package. The described processes may be implemented as instructions represented in source code, object code, and/or machine code. These instructions may be executed directly by hardware processor(s) 210, or alternatively, may be executed by a virtual machine operating between the object code and hardware processor(s) 210.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

Furthermore, while the processes, described herein, are illustrated with a certain arrangement and ordering of subprocesses, each process may be implemented with fewer, more, or different subprocesses and a different arrangement and/or ordering of subprocesses. In addition, it should be understood that any subprocess, which does not depend on the completion of another subprocess, may be executed before, after, or in parallel with that other independent subprocess, even if the subprocesses are described or illustrated in a particular order.

2.1. Introduction

To address the problems associated with fixed scanning protocols, embodiments utilize monitored reconstruction. See, e.g., Bulatov et al., "Monitored Reconstruction: Computed Tomography as an Anytime Algorithm," IEEE Access, 8:110759-110774, 2020; and U.S. patent application Ser. No. 17/180,397, titled "Systems and Methods for Monitored Tomographic Reconstruction," filed on Feb. 19, 2021; which are both hereby incorporated herein by reference as if set forth in full. Monitored reconstruction focuses on real-time estimation of whether the information obtained during CT scanning is sufficient for an acceptable reconstruction. It should be understood that, as used herein, the term "real-time" or "in real time" refers to an event (e.g., partial CT reconstruction, classification, and application of a stopping rule) that occurs contemporaneously with another event (e.g., projection acquisition), as dictated by ordinary delays between the two events (e.g., processing and/or communication latencies), and does not require the two events to occur perfectly simultaneously.

The CT scanning process may stop at different times for different target objects, with an increase of mean effectiveness in terms of the tradeoff between the quality of the reconstructed CT image and the administered radiation dose. Mean reduction of the dose, while retaining the same mean accuracy compared to a fixed scanning protocol, has been demonstrated using the data obtained with a laboratory microtomography setup and a nano X-ray CT setup in the case of reconstructing two-dimensional sections with a random protocol for acquiring X-ray projections. See Bulatov et al. (2020); and Bulatov et al., "Monitored Tomographic Reconstruction—an Advanced Tool to Study the 3D Morphology ofNanomaterials," Nanomaterials, 11(10), 2021, art. no. 2524, which is hereby incorporated herein by reference as if set forth in full.

In an embodiment, a reduction in radiation dose is achieved during helical CT scanning by using a monitored reconstruction process that, instead of analyzing the quality of the reconstructed results using a quality metric, utilizes a pre-trained anomaly detection neural network model (e.g., COVID-19 detection neural network model) as an "expert." The scanning protocol may perform partial reconstruction of the slices of the target object volume, and, based on the neural network output for those partially reconstructed slices, decide to reduce the frequency of the projections obtained for portions of the scanning process. This can reduce the overall radiation dose, while retaining the accuracy of predictions.

Figure 1:
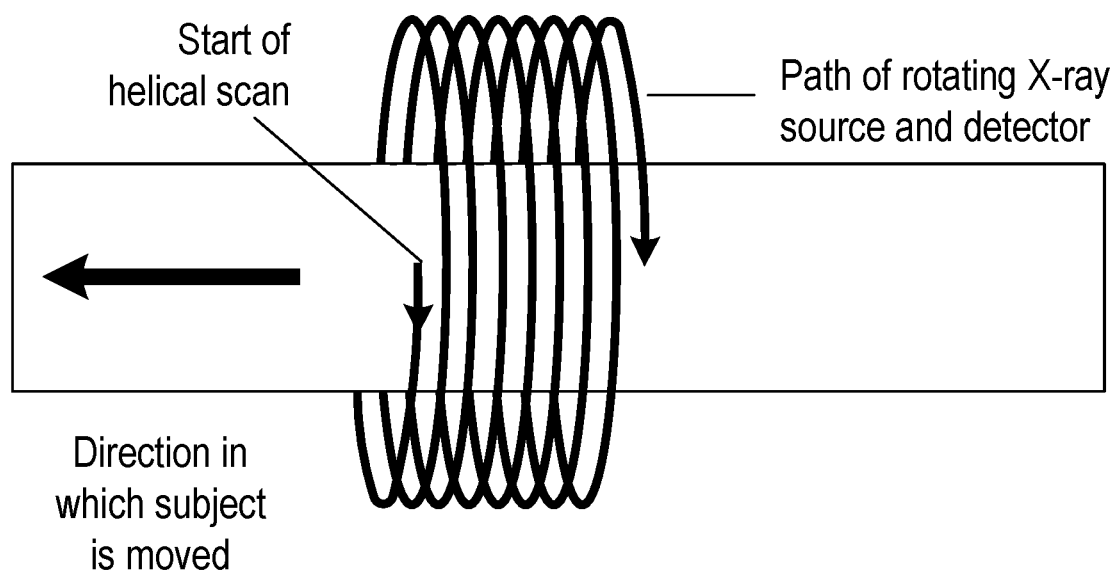
FIG. 1 illustrates helical computed tomography, according to an embodiment.
Figure 3:
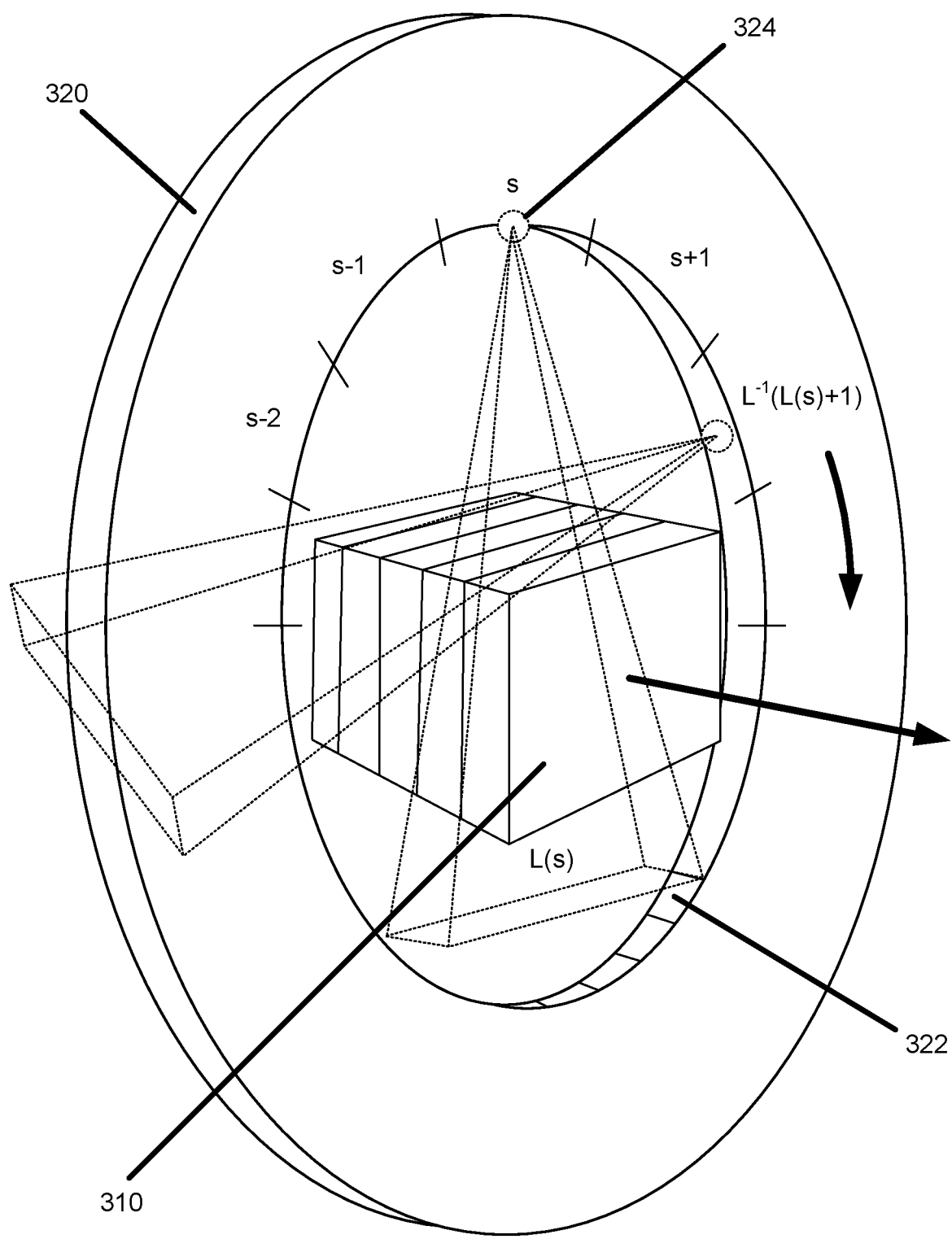
FIG. 3 illustrates a CT scanning process, according to an embodiment.

FIG. 3 illustrates a CT scanning process, according to an embodiment. It should be understood that the elements in FIG. 3 are simplified for ease of understanding. In general, a target object 310 moves relative to a detector ring 320 of a CT machine. A gantry, comprising one or more X-ray detectors 322 and an X-ray source 324 (e.g., X-ray tube) on an opposite side of the gantry from the X-ray detector(s) 322, rotates around detector ring 320 to produce projections of slices of target object 310 from a plurality of positions along a helical or spiral trajectory (illustrated in FIG. 1), as target object 310 moves through the center opening in detector ring 320. In conventional systems, target object 310 moves through detector ring 320 (e.g., on a table that is fed through detector ring 320), while detector ring 320 remains stationary. However, in an alternative system, detector ring 320 could instead move around target object 310 while target object 310 remains stationary, or both detector ring 320 and target object 310 could move (e.g., in opposite directions). Thus, when target object 310 is described herein as moving relative to detector ring 320, it should be understood that this refers to a relative change in position that may result from one or both of target object 310 and detector ring 320 moving.

As X-ray source 324 rotates around detector ring 320, a projection of a slice of target object 310 is captured by detectors 322 from each of a plurality of sectors s. In other words, the helical trajectory of X-ray source 324, relative to target object 310, is divided into S sectors s, with each sector s having the same angular length. In addition, target object 310 is divided into K slices. The number K of slices is determined by the hardware configuration, the parameters of the CT scanning process, and the reconstruction method.

In an embodiment, the CT scanning process satisfies the following four conditions:

Firstly, while X-ray source 324 is rotating inside a sector $s \in \{1, 2, \ldots, S\}$, a fixed number of projections are acquired (i.e., by X-ray detector(s) 322). The acquired projections for each sector s are added to the total set of X-ray projections that are used to perform reconstruction of the CT image.

Secondly, the set of projections acquired in a sector $s \in \{1, 2, \ldots, S\}$ influence only a limited range of slices represented by the indices [L(s), R(s)], where $1 \leq L(s) \leq R(s) \leq K$. The indices L(s) and R(s), representing the range of slices that are influenced by the projections acquired in a sector s, may be calculated from experimental geometry, such that they are known in advance for each sector (e.g., recorded in a lookup table or other data structure stored in main memory 215 and/or secondary memory 220, implemented in an algorithm executed by processor(s) 210, etc.). In addition, for each slice k, the index of the earliest sector s whose projections influence the reconstruction of slice k, is known in advance (e.g., recorded in a lookup table or other data structure stored in main memory 215 and/or secondary memory 220, implemented in an algorithm executed by processor(s) 210, etc.). In other words, for each slice k, the sector s with the smallest index, such that L(s)=k, can be quickly determined. The index of this sector s can be denoted $L^{-1}(s)$. Thus, L(s) receives a sector index as an input, and outputs the slice index of the first slice (e.g., lowest slice index), along the scanning path, that is influenced by the sector at the inputted sector index. Conversely, $L^{-1}(s)$, which is the inverse function of L(s), receives a slice index as an input, and outputs the sector index of the first sector (e.g., lowest sector index), along the helical scanning trajectory, that influences the slice at the inputted slice index.

Thirdly, during the CT scanning process, the frequency of projection acquisition for each sector can be dynamically changed before the projection acquisition in that sector has begun. In particular, there are at least two modes of projection acquisition: (i) a full mode, in which the maximum number (e.g., set in advance with the scanning protocol) of projections are acquired in a sector s; and (ii) a reduced mode, in which less than the maximum number of projections are acquired in a sector s (i.e., only a partial subset of the projections are acquired, relative to the full mode). Importantly, in the reduced mode, since fewer projections are acquired, the radiation dose to which target object 310 is exposed is reduced relative to the full mode. In an alternative embodiment, the reduced mode may acquire projections in some other way that reduces the radiation dose relative to the full mode. For example, the reduced mode may acquire the same number of projections as the full mode, but with a shorter exposure time per projection than the full mode. Thus, more generally, the reduced mode subjects a target object to a lower radiation dose than the full mode, at the expense of the quality of the reconstruction result.

Fourthly, for each slice k, an intermediate reconstruction result can be obtained at any time using the current accumulation of projections that influence that slice k. In addition, for each reconstruction result, whether partial or full, a classification result $C(k) \in [0,1]$, can be obtained. Each classification result C(k) can be interpreted as a membership estimation for a disease or other anomaly class. For example, the classification result C(k) may represent an estimation that slice k exhibits COVID-19. However, it should be understood that the classification result may represent a membership estimation for a different disorder or anomaly or other sets of classes.

2.2. Scanning Protocol

Figure 4:
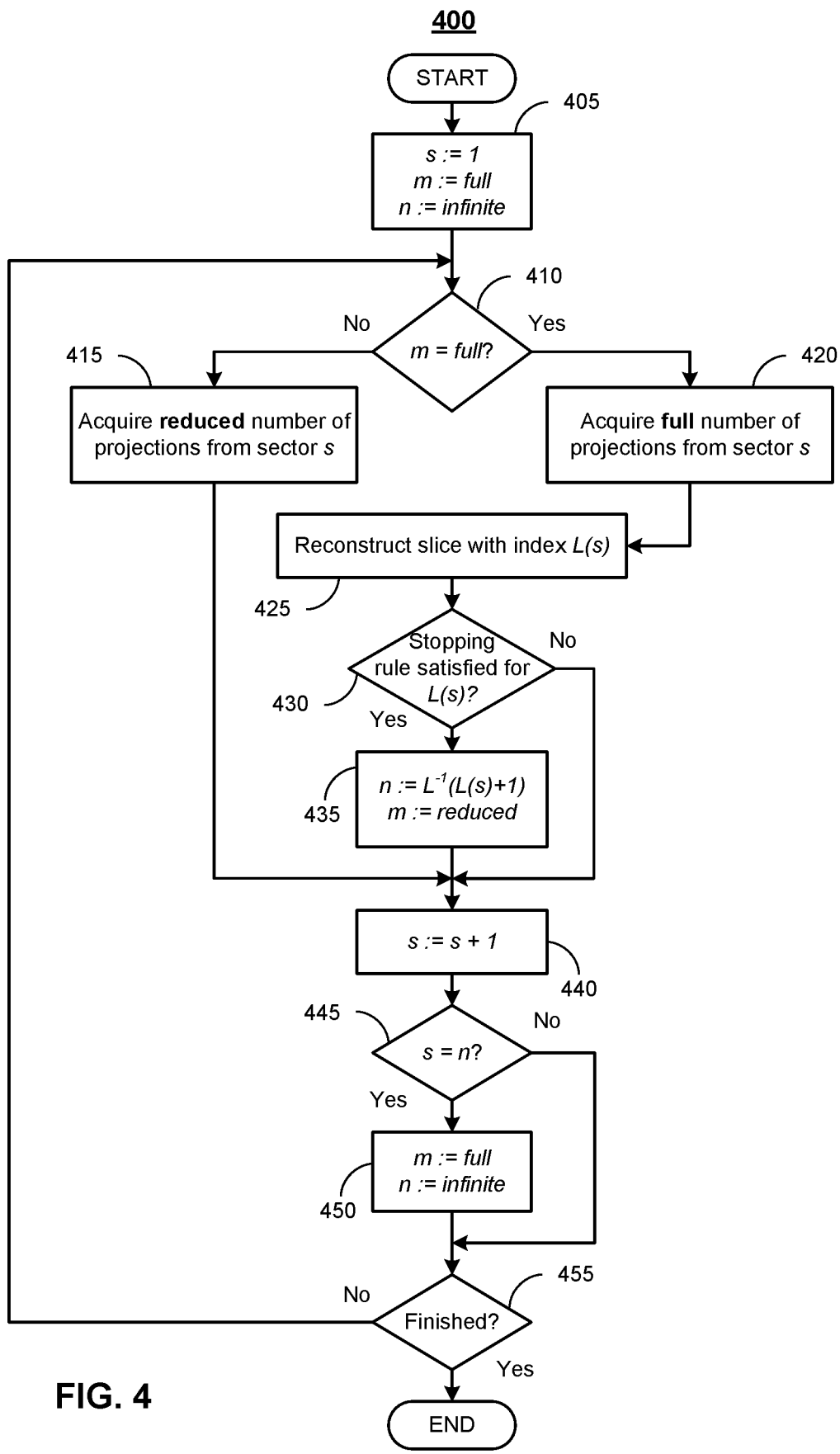
FIG. 4 illustrates an example scanning protocol for reducing a radiation dose to a target object using automatic per-slice classification, according to an embodiment.

FIG. 4 illustrates an example scanning protocol 400 for reducing a radiation dose to a target object using automatic per-slice classification, according to an embodiment. At a high level, protocol 400 utilizes a per-slice stopping rule, comprising one or more stopping criteria, to switch between a full mode, which exposes the target object to a normal radiation dose, and a reduced mode, which exposes the target object to a reduced radiation dose. The variable s represents the current sector for which projections are acquired, the variable m represents the current projection acquisition mode (i.e., either the full mode or the reduced mode), and the variable n represents the index of the next sector to be processed in the full mode.

In subprocess 405, the variables used by protocol 400 are initialized. In an embodiment, the current sector s is initialized to the first sector in the entire helical scanning trajectory, and the current mode m is initialized to the full mode. Thus, protocol 400 starts from the first sector and in the full mode. In addition, the index n of the next sector to be processed in the full mode may be set to a value representing infinity. It should be understood that the value representing infinity may be any value that does not correspond to an index of a valid sector (e.g., the largest number that can be represented by the data type used for the variable n, or otherwise well above the highest sector index).

In subprocess 410, it is determined whether the current mode m is the full mode. If the current mode m is the reduced mode (i.e., "No" in subprocess 410), protocol 400 acquires a reduced number of projections from current sector s in subprocess 415. Otherwise, if the current mode m is the full mode (i.e., "Yes" in subprocess 410), protocol 400 acquires the full number of projections from current sector s in subprocess 420. In other words, a full or reduced set of projections are acquired based on the current projection acquisition mode, as indicated by the current value of variable m.

In the event that a full number of projections are acquired from sector s (i.e., subprocess 420 is performed), the slice at index L(s) is partially reconstructed in subprocess 425. Then, in subprocess 430, it is determined whether or not the stopping rule, comprising one or more stopping criteria, is satisfied for the slice at index L(s). If the stopping rule is satisfied for the slice at index L(s) (i.e., "Yes" in subprocess 430), protocol 400 sets the index n of the next slice to be processed in the full mode to $L^{-1}(L(s)+1)$, and sets the projection acquisition mode m to the reduced mode. In this case, $L^{-1}(L(s)+1)$ is the index of the first sector that influences the slice that immediately follows the slice at index L(s). Otherwise, if the stopping rule is not satisfied for the slice at index L(s) (i.e., "No" in subprocess 430), protocol 400 proceeds to the next sector in subprocess 440, without modifying variables n or m. In particular, in subprocess 440, the index of the current sector s is incremented by a value of one.

On the other hand, in the event that a reduced number of projection are acquired from sector s (i.e., subprocess 415 is performed), protocol 400 proceeds to the next sector in subprocess 440. Thus, after the stopping rule is satisfied in an iteration of subprocess 430, projections in all subsequent sectors that influence the slice at index L(s) will be acquired in the reduced mode. In other words, the reduced mode will be maintained until the next slice (i.e., at index L(s)+1).

In subprocess 445, it is determined whether or not the value of the current sector s is equal to the value of index n. If the value of the current sector s is equal to the value of index n (i.e., "Yes" in subprocess 445), the current mode m is reset to the full mode, and the index n is reset to the initial value (e.g., the same value as in subprocess 405, such as the value representing infinity), in subprocess 450. Then, protocol 400 proceeds to subprocess 455. Otherwise, if the value of the current sector s is not equal to the value of index n (i.e., "No" in subprocess 445), protocol 400 proceeds to subprocess 455 without resetting variables m or n.

In subprocess 455, it is determined whether or not the CT scanning process is complete (e.g., the entire desired portion of target object 310 has been acquired). If the CT scanning process is complete (i.e., "Yes" in subprocess 455), protocol 400 may end. Otherwise, if the CT scanning process is not complete (i.e., "No" in subprocess 455), protocol 400 returns to subprocess 410 to acquire projections from the next sector in the mode indicated by the value of current mode m.

Notably, the reduced frequency of projection acquisition in some of sectors s (i.e., in one or more iterations of subprocess 415), initiated by the satisfaction of the stopping rule for one or more partially reconstructed slices (i.e., in one or more iterations of subprocess 430), reduces the radiation dose to which target object 310 is exposed. This monitored approach uses a per-slice stopping rule that depends on the partial reconstruction results for a slice to reduce the overall radiation dose to target object 310 without a significant decrease in classification accuracy.

2.3. Example Per-Slice Stopping Rule

Each slice either contains a set of features indicating the target anomaly (e.g., COVID-19) or does not contain a set of features indicating the target anomaly. Thus, the per-slice ground truth may be represented as a single number $\theta \in \{0, 1\}$, where 0 means that the slice does not present features indicating the target anomaly, and 1 means that the slice does present features indicating the target anomaly.

During protocol 400, each batch of projections, acquired in full mode by subprocess 420, can be used to produce a partial reconstruction in subprocess 425. A partial reconstruction refers to the reconstruction of a slice into a CT image from only a portion of the projection data acquired for that slice. The consecutive addition of new projection data should increase the CT image quality and decrease the amount and intensity of reconstruction artifacts in the CT image. Thus, sectors acquired in full mode should supply more information than sectors acquired in reduced mode. However, sectors acquired in full mode will also result in exposing target object 310 to a higher dose of radiation than sectors acquired in reduced mode.

In subprocess 430, each partial reconstruction (e.g., from subprocess 425) may be passed as an input to a classification model, which may comprise a classification neural network, other type of classifier, or an ensemble of such classifiers. Over iterations of this classification in subprocess 430, a sequence of classifications $C_1, C_2, \ldots, C_n, \ldots$, representing network responses, will be obtained, in which $C_i \in [0,1]$, representing the value of the membership estimation for the anomaly class (e.g., COVID-19 class). If a reconstruction is stopped after n sectors, the total loss may be calculated as the sum of the classification error and the total cost of the obtained projections. Assuming that the total number of projections after processing n sectors is denoted as p(n) and each projection has a fixed cost γ, this loss can be expressed as:

$$\text{Loss}_n = \|C_n - \theta\|_2 + \gamma \cdot p(n)$$

The task of constructing a stopping rule for subprocess 430 is to determine the stopping time N that minimizes the expected total loss $E(\text{Loss}_N)$, based on the previously obtained observations. Since this problem does not comply with the monotone stopping problem, the method discussed in Bulatov et al. cannot be directly applied.

To analyze the dynamics of the predicted classifications $C_1, C_2, \ldots, C_n$ by a neural network, a random subset of slices with equal thickness (e.g., 6 millimeters) were selected from the COVID-CTset dataset, as described in Rahimzadeh et al. For each original reconstruction, the projections were simulated from the full data. Each slice had a limited number of projections that could influence its reconstruction. This number of projections may be referred to as the "lifespan" of the slice, and can be directly calculated from the geometry of the experiment. In this particular case, the lifespan of the slice consisted of 500 projections. Thus, with a sector size of 10 projections, the lifespan of the slice consisted of 50 sectors. In the experiment, random consecutive sectors were excluded from the set of sectors comprising the lifespan of each slice, and the slice was then partially reconstructed from the non-excluded sectors (i.e., activated sectors). The FPN model was used on the partial reconstructions of CT images to obtain a potential "history" of predictions $C_1, C_2, \ldots, C_n$ for each slice. This was done on 80 slices, consisting of an even distribution between negative final predictions and positive final predictions by the FPN model.

Figure 5A:
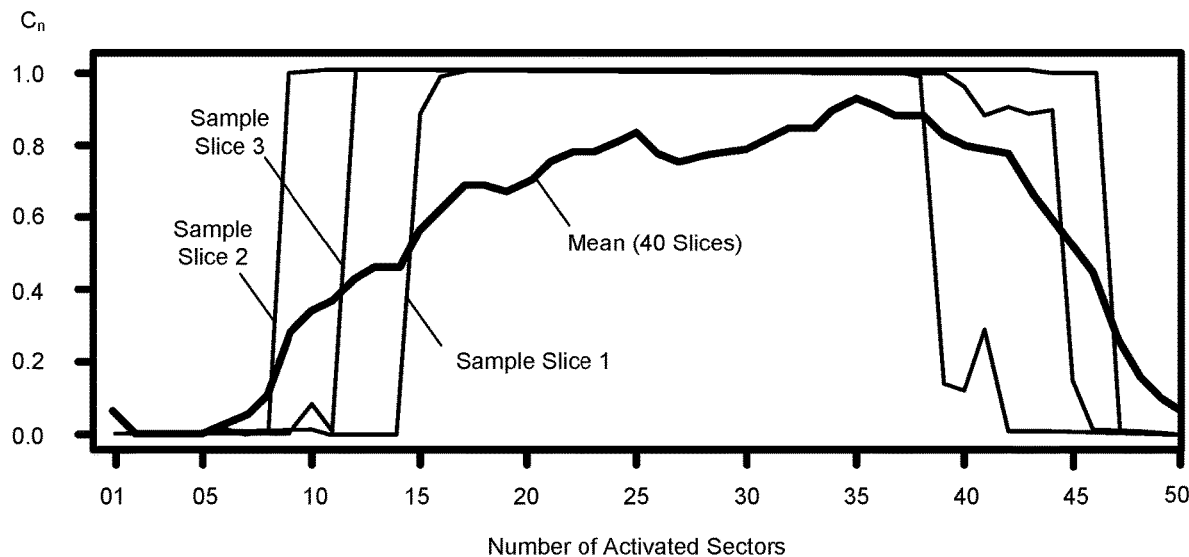
FIGS. 5A and 5B illustrate the dynamics of per-slice classification, according to an example experiment.
Figure 5B:
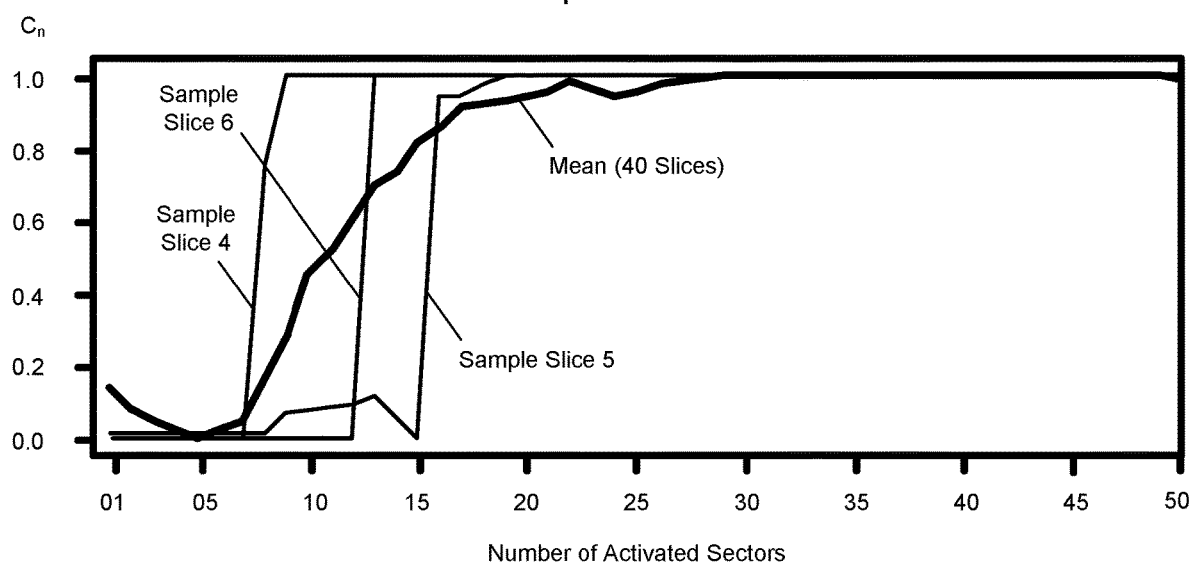

FIGS. 5A and 5B illustrate the dynamics of per-slice FPN predictions against the scale of the increasing number of activated sectors for, given a full reconstruction, slices that do not exhibit COVID-19 features (i.e., negative slices) and slices that do exhibit COVID-19 features (i.e., positive slices), respectively, according to an example experiment. Each of FIGS. 5A and 5B illustrates the dynamics of three examples slices, as well as the mean response across all negative and positive slices, respectively. Notably, there is a pattern to the responses. In particular, for both the negative and positive slices, when there are only a few activated sectors, the FPN output corresponds to the non-anomaly class representing no COVID-19. However, as the number of activated sectors increases, the FPN output quickly jumps towards the anomaly class representing the presence of COVID-19. This jump presumably represents a specific response of the FPN to artifacts present in the partial reconstructions. As the number of activated sectors further increases, the dynamics differ for negative and positive slices. For the negative slices, the FPN output eventually quickly returns to the non-anomaly class representing no COVID-19, presumably as the influence of artifacts subsides. For the positive slices, the FPN output continues to correspond to the anomaly class representing COVID-19.

In view of the observed pattern, two per-slice stopping rules were evaluated. The first stopping rule that was evaluated does not utilize monitoring. In contrast, the second stopping rule that was evaluated relies on partial reconstruction results, and therefore, does utilize monitoring.

The first stopping rule comprises stopping the analysis of a slice when the number of projections from sectors that influence the slice reaches a cut-off threshold X:

$$N_1(X) = X$$

This first stopping rule does not require monitoring. In other words, no real-time reconstructions need to be performed. Thus, a protocol that utilizes this first stopping rule, while capable of reducing a radiation dose, represents a fixed scanning protocol.

The second stopping rule utilizes a cut-off threshold X, a prediction threshold P, and a stopping threshold T:

$$N_2(X, P, T) = \max\{X, T + n_s(P)\}$$

$$n_s(P) = \begin{cases} -\infty, & \text{if } \max\{C_n\} \leq P; \\ \min\{n: C_n > P\}, & \text{otherwise} \end{cases}$$

In other words, if the membership estimation that is output by the neural network model for a slice (e.g., representing a probability that the partially reconstructed slice L(s) from subprocess 425 belongs to a class) does not exceed the prediction threshold P during acquisition of the first X sectors for that slice, the stopping rule is satisfied for the slice (i.e., "Yes" in subprocess 430) after X sectors have been acquired. Consequently, protocol 400 switches to the reduced mode (e.g., in subprocess 435) for that slice once X sectors have been acquired. Otherwise, if the membership estimation that is output by the neural network model for the slice spikes above the prediction threshold P at any point during acquisition of the first X sectors for that slice, protocol 400 switches to the reduced mode (e.g., in subprocess 435) after T sectors have been acquired following the sector $n_s(P)$ during which the first such spike was observed, but not before X sectors have been acquired. Notably, this second stopping rule requires monitored reconstruction of the slices of target object 310 (e.g., in subprocess 425), in order to generate the sequence of predictions $C_1, C_2, \ldots, C_n$ (e.g., in subprocess 430).

Figure 6:
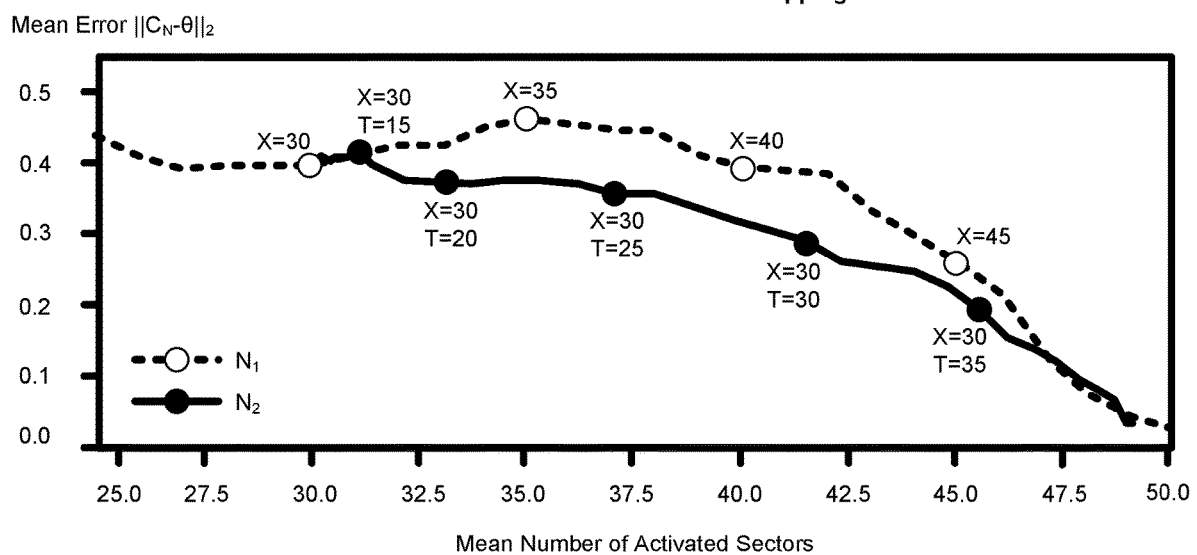
FIG. 6 illustrates performance profiles for implementations of unmonitored and monitored per-slice stopping rules, according to an embodiment.

FIG. 6 illustrates performance profiles for implementations of unmonitored per-slice stopping rule $N_1$ and monitored per-slice stopping rule $N_2$, with the vertical axis denoting per-slice accuracy, according to an embodiment. In the illustrated example, the value of X was varied for $N_1$. For $N_2$, X=30, P=0.8, and the value of T was varied. Profile points have been added to illustrate relevant threshold values. As illustrated by the performance profiles, the mean prediction error for a given slice at a given stopping point depends on the mean number of activated sectors that were used to reconstruct the slice. Comparing the curves of the performance profiles, a lower point in the curve for one stopping rule indicates a higher efficiency than the other stopping rule, either because of a lower mean prediction error given the same mean number of activated sectors or the same mean prediction error given a lesser mean number of activated sectors. Thus, the performance profiles demonstrate that the performance of monitored stopping rule $N_2$ surpasses unmonitored stopping rule $N_1$ for a certain range of T (e.g., T=20 to 35). It should be understood that further performance improvements may be achieved with different values of X and/or P.

3. Experimental Results

For experimentation, the openly available COVID-CTset dataset was used for the projections processed by protocol 400, and the pretrained classification neural network, FPN, was used for COVID-19 classification in subprocess 430. However, it should be understood that, in operation, protocol 400 will generally be applied to projections acquired in real-time during a CT scanning process. In addition, any suitable classification model (e.g., comprising a classification network, other classifier, or ensemble of such classifiers) may be used in place of FPN to classify slices in subprocess 430 (e.g., Xception or ResNet50 v2), and for any target anomaly.

The COVID-CTset dataset contains 63,849 images from 377 patients, including 95 COVID-19 patients and 282 healthy persons. The images are three-dimensional lung CT images. For each patient, there are up to 3 reconstructions with slices of different thicknesses (e.g., 1.5 to 8 millimeters) produced from the same projections.

In order to model and evaluate protocol 400, the source data should be obtained, such that reconstructions can be performed with a variable number of projections. However, this source data is not available in the COVID-CTset dataset, and is not generally available in any open data repository. Thus, for the experiments, synthetic projections were created from the reconstructions in the COVID-CTset dataset. The information necessary to reproduce the projection acquisition process (e.g., setup geometry, patient metadata, scanning protocol, model of the CT scanner, etc.) was available in the COVID-CTset dataset. However, there was no information for the number of projections per rotation. Thus, this value was selected to be half of the maximum available magnitude for the model of CT scanner (e.g., 600 out of 1200 projections per rotation). This selection was empirically derived to be close to the minimum value at which reconstructions can be performed without serious loss of quality. The collection of projections and the subsequent reconstruction were performed using Astra-Toolbox v1.9.9dev. See Palenstijn et al., "Performance Improvements for Iterative Electron Tomography Reconstruction Using Graphics Processing Units (GPUs)," Journal of Structural Biology, 176(2):250-253, 2011; Aarle et al., "Fast and Flexible X-ray Tomography Using the Astra Toolbox," Opt. Express, 24(22):25129-25147, October 2016; and Aarle et al., "The Astra Toolbox: A Platform for Advanced Algorithm Development in Electron Tomography," Ultramicroscopy, 157:35-47, 2015; which are all hereby incorporated herein by reference as if set forth in full. The Feldkamp, Davis, and Kress (FDK) algorithm was used as a starting reconstruction point for the Simultaneous Iterations Reconstruction Technique (SIRT) algorithm with 500 iterations. See Gilbert, "Iterative Methods for the Three-Dimensional Reconstruction of an Object from Projections," Journal of Theoretical Biology, 36(1):105-117, 1972, which is hereby incorporated herein by reference as if set forth in full.

The adequacy of the described modeling process and the sustainability of the pretrained neural network model to the described modeling process was validated by simulating the whole dataset and reproducing the results in Rahimzadeh et al. on the simulated data. While the modeling process yielded reconstructed slice images with slightly lower quality than the original COVID-CTset dataset, the FPN response differed for only 200 slices (i.e., 0.48% of the full COVID-CTset dataset).

To quantitatively evaluate protocol 400, a subset of the simulated data, consisting of a total of 229 slices, was extracted for 6 randomly selected patients—three of whom exhibited COVID-19, and three of whom did not exhibit COVID-19. Alternative implementations of protocol 400 were applied to this subset using both the unmonitored stopping rule $N_1$ and the monitored stopping rule $N_2$ within a range of control parameters. The reduced mode corresponded to 20% fewer projections per sector than the full mode, and the full mode consisted of acquiring 10 projections. The control parameters were chosen in accordance with the properties of the experimental geometry. The lifespan of a slice consisted of 50 sectors, which meant that a cut-off threshold X≥50 would effectively result in always taking a full set of projections from all sectors, regardless of the mode. For the monitored stopping rule $N_2$, a cut-off threshold X=30, a prediction threshold P=0.8, and a stopping threshold T selected from the value range [10, 30] were used.

After modeling protocol 400 for each patient, the per-slice prediction accuracy was measured, along with the reduction in radiation dose (expressed in a relative number of performed projections) relative to a fixed protocol in which all sectors are activated with a full dose. In particular, the accuracy was calculated as the mean ratio of the per-slice predictions that coincide with the predictions obtained with a full dose, and the dose was calculated as the mean ratio of the acquired projections to the number of projections that would be acquired if all sectors were acquired in the full mode. The resulting measurements for protocol 400 are depicted in the table below:

| Stopping Rule | Parameter Value | Accuracy (%) | Dose (%) |
| --- | --- | --- | --- |
| Unmonitored ($N_1$) | X = 30 | 89.1 | 68.2 |
|  | X = 35 | 93.5 | 78.2 |
|  | X = 40 | 96.1 | 87.4 |
|  | X = 45 | 97.4 | 95.4 |
| Monitored ($N_2$) | T = 10 | 89.1 | 68.4 |
|  | T = 15 | 93.9 | 75.5 |
|  | T = 20 | 96.5 | 81.8 |
|  | T = 30 | 98.6 | 86.9 |

The results demonstrate that the monitored stopping rule $N_2$ exhibits Pareto improvement over the unmonitored stopping rule $N_1$. In particular, the monitored stopping rule $N_2$, with T=15, T=20, or T=30, all achieve higher mean per-slice accuracy and lower mean administered dose than the unmonitored stopping rule $N_1$ with X=35, X=40, and X=45, respectively. Notably, the monitored stopping rule $N_2$ with a stopping threshold T=30 achieved a per-slice prediction accuracy of 98.6%, relative to full projection acquisition, with a mean dose reduction of 13.1%, whereas the unmonitored stopping rule $N_1$ was not able to achieve such accuracy even with a mean dose reduction of less than 5%.

The reductions in per-slice prediction accuracy and dose for each of the six patients for which the modeling was performed are depicted in the table below, with changes in accuracy and radiation dose represented in percentages (%) relative to a CT scanning process with no reduced mode:

|  | $N_1$ (X = 40) | | $N_1$ (X = 45) | | $N_2$ (T = 20) | | $N_2$ (T = 30) | |
| --- | --- | --- | --- | --- | --- | --- | --- | --- |
| Patient | Accuracy | Dose | Accuracy | Dose | Accuracy | Dose | Accuracy | Dose |
| Positive$_1$ | −8.6 | −12.1 | −5.7 | −4.0 | −5.7 | −12.1 | −5.7 | −5.0 |
| Positive$_2$ | 0.0 | −12.1 | −2.9 | −4.0 | 0.0 | −20.6 | 0.0 | −15.1 |
| Positive$_3$ | 0.0 | −12.4 | 0.0 | −4.3 | −2.5 | −12.3 | 0.0 | −5.0 |

-continued

|  | $N_1$ (X = 40) | | $N_1$ (X = 45) | | $N_2$ (T = 20) | | $N_2$ (T = 30) | |
|---|---|---|---|---|---|---|---|---|
| Patient | Accuracy | Dose | Accuracy | Dose | Accuracy | Dose | Accuracy | Dose |
| Negative$_1$ | −7.5 | −14.2 | −5.0 | −6.6 | −5.0 | −23.5 | 0.0 | −21.1 |
| Negative$_2$ | −4.7 | −12.3 | −2.3 | −4.2 | −7.0 | −23.5 | −2.3 | −17.7 |
| Negative$_3$ | −2.8 | −12.3 | 0.0 | −4.2 | 0.0 | −15.7 | 0.0 | −13.3 |

As illustrated, the improvement of monitored stopping rule $N_2$ over unmonitored stopping rule $N_1$ was more significant in the case of patients with COVID-19. Presumably, this is due to the fact that, on some slices without COVID-19 features, the FPN does not change its output at all, in which case the monitored stopping rule $N_2$ stops earlier, resulting in a larger dose reduction. However, it should be understood that such slices can occur in both COVID-19 and non-COVID-19 patients, but will typically occur at a higher frequency in non-COVID-19 patients.

Notably, with the unmonitored stopping rule $N_1$, the dose reduction is virtually the same across all patients, whereas the monitoring stopping rule $N_2$ resulted in different dose reductions for different patients. In addition, not only does the monitored stopping rule $N_2$ with a stopping threshold T=30 achieve Pareto improvement over a fixed protocol, but it also achieves Pareto improvement for each of the six evaluated patients, with a maximum reduction in per-slice prediction accuracy of 5.7% and a dose reduction in the range of 5.0% to 21.1%.

As mentioned above, the experiment used a pre-trained per-slice classifier FPN. This was purposeful to determine whether it is possible to apply the variable-dose protocol 400 with real-time monitored reconstruction without having to retrain the classification network. The results above demonstrate that neural-network-based methods of tomographic image analysis enable the construction of new and effective scanning protocols with decreased radiation doses, by using the neural network as an "expert" to judge whether or not there is sufficient diagnostic information in a partial reconstruction. Practically, protocol 400 could benefit from a custom trained per-slice classifier, which may be robust against artifacts that appear due to partial reconstruction, as well as a more sophisticated stopping rule that is designed to further increase the amount of dose reduction. However, the particular implementation of protocol 400 should account for the speed of current helical CT reconstruction algorithms, to ensure that protocol 400 does not become a prohibitive bottleneck to the overarching CT scanning process. In any case, protocol 400 represents an application of computer vision in medical imaging setups with automated diagnostics, as well as a tool for decision support systems in which the final diagnostic decision is made by a medical professional.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

What is claimed is:

1. A method comprising using at least one hardware processor to, during helical computed tomography (CT) scanning of a target object, after acquiring a set of projections from a sector in a full mode which subjects the target object to a first radiation dose:
   identify a slice of the target object that is influenced by the sector;
   reconstruct a CT image of the identified slice using projections that have been previously acquired for the slice;
   determine whether or not a stopping rule is satisfied based on the reconstructed CT image; and,
   when determining that the stopping rule is satisfied,
      switch from the full mode to a reduced mode which subjects the target object to a second radiation dose, wherein the second radiation dose is less than the first radiation dose, and
      acquire a set of projections from at least one subsequent sector in the reduced mode.

2. The method of claim 1, further comprising using the at least one hardware processor to, when determining that the stopping rule is satisfied, determine a next sector that corresponds to a next slice of the target object, wherein acquiring a set of projections from at least one subsequent sector in the reduced mode comprises acquiring a set of projections from each subsequent sector in the reduced mode until the determined next sector, and switching from the reduced mode to the full mode prior to acquiring a set of projections from the determined next sector.

3. The method of claim 2, wherein determining a next sector that corresponds to a start of a next slice of the target object comprises identifying a lowest indexed sector that influences the next slice.

4. The method of claim 1, wherein identifying a slice of the target object that is influenced by the sector comprises identifying a first slice, along a trajectory of the helical CT scanning, in a range of slices that are influenced by the sector based on a geometry of the helical CT scanning.

5. The method of claim 1, wherein determining whether or not a stopping rule is satisfied based on the reconstructed CT image comprises:

applying a classification model to the reconstructed CT image to produce a membership estimation representing a probability that the reconstructed CT image is a member of one of a plurality of classes; and determining whether or not the stopping rule is satisfied based on the membership estimation.

6. The method of claim 5, wherein determining whether or not the stopping rule is satisfied based on the membership estimation comprises:

when the membership estimation exceeds a prediction threshold at least once within an initial subset of sectors consisting of a first threshold number of sectors, determining that the stopping rule is satisfied when the first threshold number of sectors have been acquired; and, when the membership estimation never exceeds the prediction threshold within the initial subset of sectors, determining that the stopping rule is satisfied when a second threshold number of sectors have been acquired following an initial sector for which the membership estimation of the reconstructed CT image exceeds the prediction threshold.

7. The method of claim 5, wherein the plurality of classes comprises a first class representing an absence of an anomaly, and a second class representing a presence of an anomaly.

8. The method of claim 7, wherein the anomaly is COVID-19.

9. The method of claim 8, wherein the target object comprises at least one lung of a subject.

10. The method of claim 5, wherein the classification model comprises a neural network.

11. The method of claim 10, wherein the neural network is a deep-learning neural network.

12. The method of claim 10, wherein the neural network is a Feature Pyramid Network (FPN).

13. The method of claim 1, wherein the full mode acquires a first number of projections, and the reduced mode acquires a second number of projections that is less than the first number.

14. The method of claim 13, wherein the second number is at least 20% less than the first number.

15. The method of claim 1, wherein the full mode acquires each projection using a first exposure time, and the reduced mode acquires each projection using a second exposure time that is shorter than the first exposure time.

16. A system comprising:
at least one hardware processor configured to control a scanning mode of a computed tomography (CT) scanner; and software that is configured to, when executed by the at least one hardware processor, during helical CT scanning of a target object, after acquiring a set of projections from a sector in a full mode which subjects the target object to a first radiation dose identify a slice of the target object that is influenced by the sector, reconstruct a CT image of the identified slice using projections that have been previously acquired for the slice, determine whether or not a stopping rule is satisfied based on the reconstructed CT image, and, when determining that the stopping rule is satisfied,
switch from the full mode to a reduced mode which subjects the target object to a second radiation dose, wherein the second radiation dose is less than the first radiation dose, and acquire a set of projections from at least one subsequent sector in the reduced mode.

17. A non-transitory computer-readable medium having instructions stored therein, wherein the instructions, when executed by a processor, cause the processor to, during helical computed tomography (CT) scanning of a target object, after acquiring a set of projections from a sector in a full mode which subjects the target object to a first radiation dose:

identify a slice of the target object that is influenced by the sector;

reconstruct a CT image of the identified slice using projections that have been previously acquired for the slice;

determine whether or not a stopping rule is satisfied based on the reconstructed CT image; and, when determining that the stopping rule is satisfied,
switch from the full mode to a reduced mode which subjects the target object to a second radiation dose, wherein the second radiation dose is less than the first radiation dose, and acquire a set of projections from at least one subsequent sector in the reduced mode.

* * * * *